United States Patent
Benjelloun Mlayah et al.

(10) Patent No.: US 11,021,720 B2
(45) Date of Patent: Jun. 1, 2021

(54) PROCESS FOR PRODUCING, IN PARTICULAR ETHANOL, BY SEQUENCED ENZYMATIC HYDROLYSIS OF CELLULOSE AND HEMICELLULOSES OF A LIGNOCELLULOSIC RAW MATERIAL

(71) Applicant: COMPAGNIE INDUSTRIELLE DE LA MATIERE VEGETALE-CIMV, Neuilly sur Seine (FR)

(72) Inventors: Bouchra Benjelloun Mlayah, Pompertuzat (FR); Michel Delmas, Auzeville-Tolosane (FR)

(73) Assignee: COMPAGNIE INDUSTRIELLE DE LA MATIERE VEGETALE, Neuilly sur Seine (FR)

( * ) Notice: Subject to any disclaimer, the term of this patent is extended or adjusted under 35 U.S.C. 154(b) by 0 days.

(21) Appl. No.: 15/316,237

(22) PCT Filed: Jun. 3, 2015

(86) PCT No.: PCT/EP2015/062399
§ 371 (c)(1),
(2) Date: Dec. 5, 2016

(87) PCT Pub. No.: WO2015/185639
PCT Pub. Date: Dec. 10, 2015

(65) Prior Publication Data
US 2017/0137847 A1    May 18, 2017

(30) Foreign Application Priority Data
Jun. 5, 2014  (FR) ...................................... 1455095

(51) Int. Cl.
| | |
|---|---|
| C12P 7/10 | (2006.01) |
| C12P 19/02 | (2006.01) |
| C12P 19/14 | (2006.01) |
| C08H 7/00 | (2011.01) |
| C08H 8/00 | (2010.01) |
| C08B 37/00 | (2006.01) |
| C08B 1/00 | (2006.01) |

(52) U.S. Cl.
CPC ........ *C12P 7/10* (2013.01); *C08B 1/00* (2013.01); *C08B 37/0057* (2013.01); *C08H 6/00* (2013.01); *C08H 8/00* (2013.01); *C12P 19/02* (2013.01); *C12P 19/14* (2013.01); *C12P 2201/00* (2013.01); *C12P 2203/00* (2013.01); *Y02E 50/10* (2013.01)

(58) Field of Classification Search
None
See application file for complete search history.

(56) References Cited

U.S. PATENT DOCUMENTS 7,402,224 B1    7/2008    Avignon et al.

FOREIGN PATENT DOCUMENTS

| EP | 2 235 254 B1 | 10/2010 |
|---|---|---|
| EP | 2 336 291 A1 | 6/2011 |
| WO | 11/68494 A1 | 11/2000 |
| WO | 2009/092749 A1 | 7/2009 |
| WO | 2010/006840 A2 | 1/2010 |
| WO | 2012/049054 A2 | 4/2012 |
| WO | 2012/099967 A1 | 7/2012 |

OTHER PUBLICATIONS

Rakesh Koppram et al: "Simultaneous saccharification and co-fermentation for bioethanol production using corncobs at lab, PDU and demo scales", Biotechnology for Biofuels, Biomed Central Ltd, GB, vol. 6, No. 1, Jan. 14, 2013 (Jan. 14, 2013), pp. 2, XP021142736, ISSN: 1754-6834, DOI: 10.1186/1754-6834-6-2.

Olofsson Kim et al: "Improving simultaneous saccharification and co-fermentation of pretreated wheat straw using both enzyme and substrate feeding", Biotechnology for Biofuels, Biomed Central Ltd, GB, vol. 3, No. 1, Aug. 2, 2010 (Aug. 2, 2010), pp. 17, XP021082865, ISSN: 1754-6834.

International Search Report, dated Jul. 1, 2015, from corresponding PCT application.

*Primary Examiner* — Paul J Holland
(74) *Attorney, Agent, or Firm* — Nixon & Vanderhye

(57) ABSTRACT

A process for producing ethanol includes steps of pretreatment of the lignocellulosic vegetable raw material, including the steps consisting in destructuring the lignocellulosic vegetable raw material, then in separating, on the one hand, the cellulose (C6) capable of then being hydrolysed (and fermented for the production of ethanol) and, on the other hand, the hemicelluloses capable of then being hydrolysed and the lignins. The hydrolysis of the cellulose and of the hemicelluloses is then carried out in a sequenced manner according to the following steps consisting in:
i) beginning the enzymatic hydrolysis of the cellulose by at least one enzyme for a first period with a view to obtaining an intermediate hydrolysate;
ii) adding hemicelluloses to the intermediate hydrolysate;
iii) continuing the enzymatic hydrolysis of the mixture until a final hydrolysate is obtained at the end of a total period of enzymatic hydrolysis.

15 Claims, 1 Drawing Sheet

Figure 1:
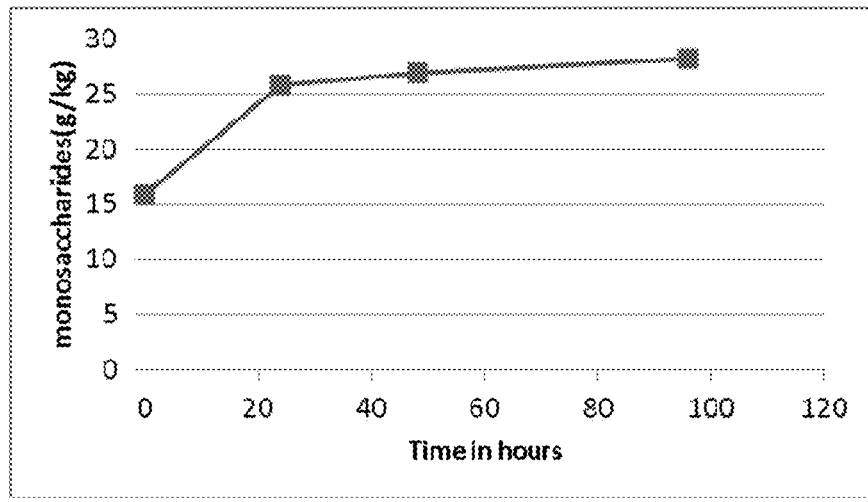

PROCESS FOR PRODUCING, IN PARTICULAR ETHANOL, BY SEQUENCED ENZYMATIC HYDROLYSIS OF CELLULOSE AND HEMICELLULOSES OF A LIGNOCELLULOSIC RAW MATERIAL

The present invention relates to a process for producing in particular ethanol, comprising a pre-treatment of the lignocellulosic vegetable raw material (MPVL) in order to separate the cellulose, the hemicelluloses and the lignins, and comprising an enzymatic hydrolysis of the C5 polysaccharides (pentoses) and C6 polysaccharides (hexoses).

Generally, the compositions of the various sources of biomasses exhibit great heterogeneity in terms of anatomies and structures, but they also exhibit a degree of invariance, namely the presence of three major macromolecular compounds, cellulose, hemicelluloses and lignins.

Cellulose is a linear glucose polymer, and therefore a potential source of fermentable sugars; hemicelluloses are heteropolymers, the most represented monomers of which are C5 sugars comprising five carbon atoms (xylose, arabinose) which are easily metabolised by numerous microorganisms; while lignins are complex three-dimensional heteropolymers, the natural degradation of which is a long complex process and for which it is to date considered that it would be illusory to want to derive therefrom any industrial production process by hydrolysis.

The specificity of lignocelluloses requires, in particular for the purpose, for example, of producing ethanol from the fermentable sugars mentioned above, carrying out a pre-treatment for sorting out the problem of accessibility of the cellulose to enzymatic reagents aiming in particular to solubilise the hemicelluloses and lignins.

The applicant, CIMV, is a company specialising in the treatment and exploitation of lignocellulosic vegetable raw material.

In this regard, the applicant has filed and is the proprietor of various patent applications and patents relating to a process for producing paper pulp, lignins, sugar and acetic acid by fractionation of lignocellulosic vegetable material in a formic acid/acetic acid medium (WO-A1-00/68494).

The applicant is also the proprietor of patent applications and/or patents relating to a process for pre-treating a lignocellulosic vegetable material for producing bioethanol (WO-A2-2010/006840).

Such a pre-treatment process makes it possible in particular to obtain, from the lignocellulosic vegetable raw material (MPVL), under economic industrial conditions, firstly a substrate made up essentially of de-fibred cellulose exhibiting optimum conditions for its subsequent enzymatic hydrolysis, and a second substrate made up of sugar molasses originating from hemicelluloses, the hydrolysates of which are free of furfural.

The applicant has therefore already proposed a process for producing bioethanol from a lignocellulosic vegetable raw material, comprising the successive steps of pre-treatment of the MPVL, of enzymatic hydrolysis of the pre-treated material and of alcoholic fermentation of the products resulting from the hydrolysis step.

The applicant has in particular proposed a process for producing bioethanol from a lignocellulosic vegetable raw material, comprising the successive steps of:

a) pre-treatment of the lignocellulosic vegetable raw material in order to separate the cellulose, the hemicelluloses and the lignins contained in this lignocellulosic vegetable raw material, the pre-treatment comprising the following successive steps consisting in:

(i) destructuring the lignocellulosic vegetable raw material by placing it in the presence of a mixture containing formic acid, acetic acid and water, at a reaction temperature between 95° C. and 110° C.;

(ii) then, at atmospheric pressure and prior to any hydrolysis then fermentation action, in separating:

on the one hand, the solid phase essentially consisting of said cellulose (C6 sugars) capable of then being hydrolysed and fermented for the production of ethanol;

and on the other hand, the liquid phase containing, in particular in aqueous solution, the formic acid, the acetic acid, the lignins and the hemicelluloses (C5 sugars);

b) enzymatic hydrolysis of said solid phase;

c) alcoholic fermentation of the products resulting from said hydrolysis step, which are capable of being fermented for the production of ethanol.

This process is in particular described in detail in document EP-2 235 254 (WO-A1-2009/0927498).

This process proposes an approach that is radically different from that of the prior art, by carrying out a separation of the three biopolymers by solvolysis in an acid/water medium, which makes it possible to separate linear, non-recombined, low-molecular-weight lignins with a high added value, prior to any action of hydrolysis then fermentation of the cellulose and of the hemicelluloses.

This process makes it possible to obtain industrial performance levels regardless of the nature of the plants used, and is therefore particularly advantageous in the case of annual plants for opening the way to a new exploitation, in particular in the case of cereal straws and sugarcane bagasse or sugar sorghum bagasse, said exploitation adding to that already proposed by the applicant in International application WO-A1-00/68494 which relates to a process for producing paper pulp, lignins, sugars and acetic acid by fractionation of lignocellulosic vegetable material in a formic acid/acetic acid medium.

For example, the amount of cellulose derived from plant material (e.g. from wheat straw) by the CIMV "refining" process and the quantity of glucans which are present after enzymatic hydrolysis are as follows:

cellulosic fraction yield of the CIMV process: 48% from biomass (cereal straw case) composed of 88% of cellulose, i.e. 42% of the biomass (in weight);

glucose yield: 44% (weight ratio) of the biomass;

cellulosic alcohol yield: 21% (weight ratio) of the biomass.

The stream containing hemicelluloses, separated by the CIMV refining process, represents a potential of approximately 20% of fermentable sugars.

These inventions (CIMV processes) are aimed at improving the industrial conditions for the production of ethanol from MPVL, and in particular the hydrolysis of cellulose to give fermentable sugars.

Generally and in a known manner, the processes for producing ethanol from MPVL take into account several parameters.

Among these parameters, it has in particular been identified that lignin can be an inhibitor of enzymes and that the lignocellulosic matrix must be pre-treated in order to make the cellulose and the hemicelluloses hydrolysable.

By virtue of their chemical composition, lignin polymers are insoluble and highly reactive.

As a result, the presence of lignins reinforces the cellulose-hemicellulose network, and they hinder the penetration and the action of enzymes, requiring the presence of water.

The enzymatic hydrolysis of cellulose is a recommended approach for obtaining fermentable sugars for various reasons, and in particular because the results of economic evaluations are in favour of enzymatic hydrolysis, when it is compared with chemical hydrolysis.

Furthermore, enzymatic hydrolysis generates few effluents to be treated and no corrosion problems.

The actual enzymatic hydrolysis is carried out by simply bringing the pre-treated vegetable raw material into contact with an enzymatic solution, while ensuring that the suspension is homogeneous and that optimum conditions are maintained, said conditions being, for example for T. reesei cellulases, a temperature between 45° C. and 50° C. and a pH of about 4.8.

The enzyme action time depends on the amount of enzymes used and on the specific activity of the enzymes.

During the enzymatic hydrolysis, the reducing sugars are essentially released in the form of glucose.

The enzymes involved in cellulose degradation, which are commonly called cellulases, are of various types and of various origins and they are characterized in particular by their activity.

The cost of the cellulases is relatively high and constitutes a factor often estimated to be the most expensive in the production of bioethanol from MPVL.

As a result, considerable efforts have been made to determine the mechanism of enzymatic hydrolysis with a view to improving it, it being a complex process of the action of soluble proteins on an insoluble and "refractory" substrate.

Another parameter of the efficiency and profitability of an enzymatic hydrolysis process is the hydrolysis time, which can be relatively long, from 48 to 72 hr.

In order to improve the efficiency of the enzymatic hydrolysis of cellulose, the applicant CIMV has proposed, in document WO-A2-2012/049054, a process for producing ethanol, characterized in that it comprises, prior to the step of enzymatic hydrolysis of the cellulose, a step of partial elimination of the lignins so as to obtain a residual overall level of lignins, expressed as percentage by weight, which is non-zero and which is included in a range determined by a lower limit, and an upper limit, respectively equal to 0.30% and 4%. The overall efficiency of this method is similar, or virtually equal, to the production of the theoretical maximum level of ethanol from MPVL and, furthermore, this efficiency is the same whether the overall process makes use first of an enzymatic hydrolysis step according to the process, and then of a fermentation step, or else whether a process of simultaneous hydrolysis and fermentation (SSF process) is carried out.

Such an identical efficiency is due to the fact that the enzymatic hydrolysis of the cellulose according to this process does not produce fermentation inhibitors. In addition, it has been demonstrated that the advantages of the process (overall lignin level and specific re-acidification conditions) are not modified, i.e. are of the same nature and have the same values, regardless of the cellulases used, and regardless of whether cellulases of lesser or greater efficiency are involved.

Once the cellulose has been hydrolysed to glucose by enzymatic hydrolysis, the glucose is fermented in the same way as, for example, the glucose resulting from starch.

Known problems specific to the use of MPVL as initial substrate remain, such as the possible presence of toxic compounds and inhibitors resulting from the hemicelluloses and the lignin, and also the possibility of carrying out the enzymatic hydrolysis and the fermentation in a single step.

The inhibitors present in the hydrolysates originate from the degradation of the sugars (to furfural), from groups present in the hemicelluloses, and from the lignin.

The presence of the inhibitors depends on the nature of the MPVL and on the conditions for its pre-treatment.

In addition to the inhibition of the enzymes by furfural, combined effects of the various inhibitors have been noted.

The simultaneous implementation, in the same reactor, of the hydrolysis and fermentation operations according to a process termed SSF (Simultaneous Saccharification and Fermentation) has already been proposed, the first advantage of said process appearing to be obvious since it calls for a single apparatus, but said process requiring the use of enzymes and yeasts working in the same physicochemical environment.

However, their optimum temperatures are relatively far apart (30° C. for yeast and 50° C. for cellulases).

Thus, the development of SSF entails the development of yeast strains capable of fermenting at a much high temperature.

As regards the simultaneous fermentation and hydrolysis according to the "SSF" ("Simultaneous Saccharification and Fermentation") process which consists in carrying out the enzymatic hydrolysis and the ethanolic fermentation in a single step, the main advantages thereof are the decrease in investment by eliminating the operations required for the enzymatic hydrolysis carried out beforehand, and the absence of cellulase inhibition by glucose, which is consumed by the fermentative microorganisms as it appears.

This results in an increase in the levels and rates of hydrolysis and in the overall ethanol productivities.

Moreover, the risks of microbial contamination of the glucose-rich hydrolysate are reduced.

However, it has become apparent that the gains provided by the SSF process, in particular from the economic point of view, require certain aspects to be optimized, in particular the initial solids concentration in order to obtain high concentrations of ethanol.

According to another concept of co-fermentation, it is possible to propose combining, in a single step, the saccharification and the co-fermentation of the C5 sugars resulting from the pre-treatment with the C6 sugars generated by the enzymatic hydrolysis.

However, such an SSCF (Simultaneous Saccharification and Co-Fermentation) process requires that the abolition of the mechanisms which, in virtually all microorganisms, are in place in order to, in the presence of a mixture of sugars, systematically promote the assimilation of glucose before the assimilation of the other sugars.

Thus, two different industrial process schemes naturally emerge from the possible combinations of the various options known from the prior art.

The first scheme provides for a separation of the C5 sugars at the end of the pre-treatment step, this C5 sugar stream being fermented separately and it being possible for one fraction to optionally be used for the production of cellulases, it being possible for an insoluble fraction (cellulose+lignin) resulting from a pre-treatment to be treated by the SSF method.

A second scheme, apparently much simpler, based on SSCF, requires the availability of a microorganism (or a mixture of microorganisms) capable of fermenting C5 and C6 sugars simultaneously and with exactly the same efficiency.

This is because a difference in the metabolization rates would make it necessary to prolong the fermentation until the sugar metabolized the most slowly was exhausted, thereby resulting in under-using the whole of the industrial equipment for production, in particular for fermentation in the case of bioethanol production.

In order to take a decisive step in the feasibility and profitability of such methods, the invention proposes a novel process based, in a known manner, on a first pre-treatment part resulting in a separation of the cellulose, the hemicelluloses and the lignins and then, surprisingly, a sequenced hydrolysis of the C6 and C5 polysaccharides resulting in the obtaining of a final hydrolysate (or co-hydrolysate), in particular capable of being fermented for the production of bioethanol, or of any other product, in particular according to the yeasts used.

For this purpose, the present invention proposes a process for producing a product, such as, for example, bioethanol, from a lignocellulosic vegetable raw material (MPVL), comprising steps:

a) of pre-treatment of the lignocellulosic vegetable raw material in order to separate the cellulose (C6), the hemicelluloses (C5) and the lignins contained in this lignocellulosic vegetable raw material, the pre-treatment comprising the successive steps consisting in destructuring the lignocellulosic vegetable raw material, then in separating, on the one hand, the cellulose (C6) capable of then being hydrolysed (and fermented for the production of bioethanol) and, on the other hand, the hemicelluloses (C5 oligosaccharides) capable of then being hydrolysed;

b) of enzymatic hydrolysis of the cellulose (C6);

c) of enzymatic hydrolysis of the hemicelluloses (C5); characterized in that the hydrolysis of the cellulose and of the hemicelluloses is carried out in a sequenced manner according to the following successive steps consisting in:

i) beginning the enzymatic hydrolysis of the cellulose (C6) by means of at least one enzyme (cellulase) for a first period (T1) with a view to obtaining an intermediate hydrolysate;

ii) adding hemicelluloses (C5) to said intermediate hydrolysate;

iii) continuing the enzymatic hydrolysis of the mixture until a final hydrolysate is obtained at the end of a total period (T2) of enzymatic hydrolysis.

By way of example, for one metric tonne of straw constituting the lignocellulosic vegetable raw material, the process according to the invention makes it possible to increase by approximately 20% the amount of ethanol produced.

Thus, the advantage of "combining" in a sequenced and controlled manner the two initially distinct streams resulting from the refining of the biomass, while increasing the overall yield and eliminating a part of the equipment and of the operating costs of a production unit that would treat the two sugar streams separately, can be clearly seen.

Advantageously, and in order in particular to be able to easily implement the process, by dispensing with the problems of viscosity while at the same time working a cellulose with a high solids content, said step i) of enzymatic hydrolysis of the cellulose consists in:

i1) introducing said at least one first enzyme into a reactor;

i2) adding a first part of the cellulose until a mixture of which the solids (MS) content is between 10% and 15% by weight is obtained;

i3) leaving the mixture to hydrolyse for a period of between six hours and fifteen hours;

i4) adding the remaining part of the cellulose in several steps so as to obtain a final solids (MS) content of between 20% and 25% by weight.

Said first period (T1) of enzymatic hydrolysis of the cellulose is between twenty hours and forty hours according to the enzyme, or the mixture of enzymes, used.

Said first step i) of enzymatic hydrolysis of the cellulose is, for example, carried out at a temperature of between 45° C. and 55° C.

The solids content of the cellulose is between 10% and 25%.

The solids content of the cellulose is preferably greater than 20%.

Said step ii) of adding the hemicelluloses is carried out in a single step, after introduction of all of the cellulose to be hydrolysed.

Said step ii) of adding the hemicelluloses further consists in simultaneously adding another enzyme, in particular capable of hydrolysing the hemicelluloses.

Said step iii) consisting in continuing the enzymatic hydrolysis is carried out at a temperature of between 45° C. and 55° C.

The solids content of the hemicelluloses is between 20% and 35% by weight.

The total period (T2) of sequenced enzymatic hydrolysis of the cellulose and of the hemicelluloses is between forty-eight hours and seventy-two hours.

Said at least one enzyme is an enzyme capable of hydrolysing cellulose, in particular a cellulase such as, for example, Cellic CTec™ plus Htec™ from Novozyme or CMAX™ from Dyadic.

Said at least one enzyme is a mixture of enzymes capable of hydrolysing cellulose and hemicelluloses, such as, for example, Cellic CTec™ plus Htec™ from Novozyme or CMAX™ from Dyadic.

Said other enzyme is an enzyme capable of hydrolysing hemicelluloses, such as, for example, Cellic Htec™ from Novozyme or CMAX™ from Dyadic.

The process comprises a step of at least partially eliminating the lignins from the phase containing the hemicelluloses, prior to said step ii) of adding the hemicelluloses (C5) to said intermediate hydrolysate.

The process according to the invention comprises the following successive steps consisting in:

(j) destructuring the lignocellulosic vegetable raw material by placing it in the presence of a mixture containing formic acid, acetic acid and water, at a reaction temperature between 95° C. and 110° C.;

(jj) then, at atmospheric pressure and prior to any hydrolysis action, in separating:
  on the one hand, a solid phase essentially consisting of said cellulose, constituting a first co-substrate, capable of then being hydrolysed; and
  on the other hand, a liquid phase containing, in particular in aqueous solution, the formic acid, the acetic acid, the lignins and the hemicelluloses, constituting a second co-substrate capable of then being hydrolysed after separation of the acids and of the lignins.

For the production of bioethanol, the process comprises an additional step of alcoholic fermentation of the final hydrolysate.

As mentioned above, by way of example, for one metric tonne of straw constituting the lignocellulosic vegetable raw material, the process according to the invention makes it possible to increase by approximately 20% the amount of ethanol produced.

By hydrolysing the two streams of C6 and C5 sugars, it is possible to mobilize the sugars contained in the two streams and obtain satisfactory fermentation yields.

Several possibilities to mobilize these C6 and C5 sugars were studied:

a) Hydrolysis and fermentation of separated C6 and C5 streams or flows;

b) Separate hydrolysis of the two C6 and C5 streams followed by a co-fermentation of the two co-hydrolysates;

c) Co-hydrolysis of the C6 and C5 streams, and fermentation of the co-hydrolysate.

a) Hydrolysis of cellulose+fermentation of the cellulose
Hydrolysis and fermentation of C5 oligosaccharides (sugar juice)+fermentation of xylose.

a-i) hydrolysis and fermentation of the cellulose to etha-nol, at high concentration (above 20%):

hydrolysis with a 95% yield glucose fermentation to etha-nol at a conversion rate of 0.48.

Thus reaching a total of 0.21 kg of ethanol per kg of biomass a-ii) hydrolysis and fermentation of C5 syrups: the hydrolysis of the oligosaccharides contained in the sugar juices can be carried out at less than 20% of the dry matter; the oligosaccharides hydrolysis yield is inferior to 50%: See FIG. 1.

But the fermentation of this stream of C5 sugars is not or poorly fermentable.

Indeed the fermentation of this stream necessarily involves a chromatographic purification step which permits to remove part of the yeast inhibitors. Without such purification, the sugar syrup is not fermentable.

In this case, this implies that the amount of ethanol that can be produced is the amount of ethanol obtained from the cellulosic fraction, i.e. is 21% in weight of the biomass.

Thus reaching a total of 0.21 kg of ethanol per kg of biomass b) The two streams are separately hydrolysed and co-fermented at a concentration of 20% of dry matter (MS) for each:

| Cellulose hydrolysate | Sugar juice hydrolysate | C6/C5 ratio | Fermentable sugars T = 0 (g/Kg) | Ethanol (g/Kg) | Yield |
|---|---|---|---|---|---|
| MS = 20% | MS = 17% | 65/35 | 138 | 48 | 0.36 |

In this case, the amount of ethanol produced, as well as the ethanol concentration, is relatively low.

Thus reaching a total of 0.24 kg of ethanol per kg of biomass c) Co-hydrolysis and co-fermentation of the co-hydrolysates of C6 and C5:

In the case of a co-hydrolysis, the sugar juice (C5) can be used at a concentration greater than 22%, so as to obtain the most concentrated possible co-hydrolysate; thereby the amount of fermentable sugars obtained after co-hydrolysis—in a weight ratio of 65/35—is higher than 180 g/litre and the ethanol yield is about 0.47 to 0.48 g/l.

Figure 2:
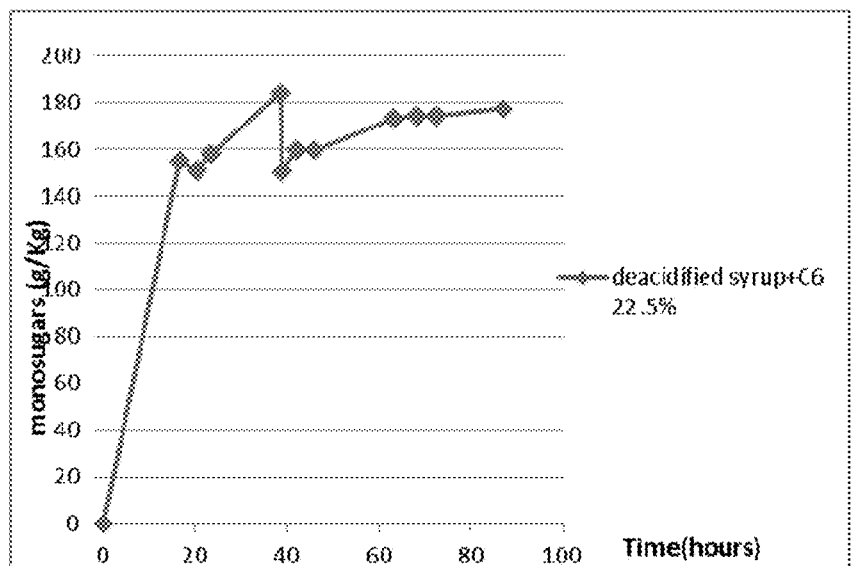

See FIG. 2.

Thus reaching a total of 0.265 kg of ethanol per kg of biomass, i.e. an increase of more than 20% of the amount of produced ethanol.

The invention claimed is:

1. A process for sequenced enzymatic hydrolysis and fermentation of a lignocellulosic vegetable raw material (MPVL), comprising the following successive steps:

a) pre-treatment of the lignocellulosic vegetable raw material in order to separate the cellulose (C6), the hemicelluloses (C5) and the lignins contained in the lignocellulosic vegetable raw material, the pre-treatment comprising successive steps consisting of destructuring the lignocellulosic vegetable raw material and separating the cellulose (C6) capable of then being hydrolysed and fermented for the production of bio-ethanol and the hemicelluloses (C5 oligosaccharides) capable of then being hydrolysed;

b) enzymatic hydrolysis of the cellulose (C6) obtained in step a);

c) enzymatic hydrolysis of the hemicelluloses (C5) obtained in step a); wherein the enzymatic hydrolysis of the cellulose and of the hemicelluloses is carried out in a sequenced manner according to the following successive steps consisting in:

i) beginning the enzymatic hydrolysis of the separated cellulose (C6) obtained in step (a) by contacting the separated cellulose (C6) with at least one enzyme for a first period (T1) thereby obtaining an intermediate cellulose hydrolysate, wherein the separated hemicellulose (C5) are not yet hydrolysed during the first time period (T1);

ii) adding the separated and not yet hydrolysed hemicelluloses (C5) obtained in step (a) to the intermediate cellulose hydrolysate obtained in step (i), thereby obtaining a mixture of not yet hydrolysed hemicelluloses (C5) and of the intermediate cellulose hydrolysate obtained in step (i);

iii) continuing the enzymatic hydrolysis of the mixture obtained in step (ii), thereby obtaining a final hydrolysate at the end of a total period (T2) of enzymatic hydrolysis; and iv) fermenting the final hydrolysate.

2. The of claim 1, wherein step i) of enzymatic hydrolysis of the cellulose consists in:

i1) introducing said at least one enzyme into a reactor;

i2) adding a first part of the cellulose until a mixture of which the solids (MS) content is between 10% and 15% by weight is obtained;

i3) allowing the mixture to hydrolyse for a period of between six hours and fifteen hours;

i4) adding the remaining part of the cellulose in several steps so as to obtain a final solids (MS) content of between 20% and 25% by weight.

3. The process of claim 1, wherein said first period (T1) of enzymatic hydrolysis of the cellulose is between twenty hours and forty hours.

4. The process of claim 1, wherein said first step i) of enzymatic hydrolysis of the cellulose is carried out at a temperature of between 45° C. and 55° C.

5. The process of claim 1, wherein the solids content of the cellulose is between 10% and 25%.

6. The process of claim 1, wherein said step ii) consists in simultaneously adding at least one other enzyme.

7. The process of claim 1, wherein said step iii) is carried out at a temperature of between 45° C. and 55° C.

8. The process of claim 1, wherein the solids content of the hemicelluloses is between 20% and 35% by weight.

9. The process of claim 1, wherein said total period (T2) of enzymatic hydrolysis is between forty-eight hours and seventy-two hours.

10. The process of claim 1, wherein said at least one enzyme is an enzyme for hydrolysis of cellulose.

11. The process of claim 1, wherein said at least one enzyme is a mixture of enzyme capable of hydrolyzing cellulose and hemicelluloses.

12. The process of claim 6, wherein said at least one other enzyme is an enzyme capable of hydrolyzing hemicelluloses.

13. The process of claim 1, further comprising, a step of at least partially eliminating the lignins from the hemicelluloses, prior to said step ii).

14. The process of claim 1, further comprising the following successive steps consisting in:
- (j) destructuring the lignocellulosic vegetable raw material by placing it in the presence of a mixture containing formic acid and water, at a reaction temperature between 95° C. and 110° C.;
- (jj) then, at atmospheric pressure and prior to any hydrolysis action, separating: a solid phase consisting essentially of said cellulose, constituting a first co-substrate, capable of then being hydrolysed and a liquid phase containing, in particular in aqueous solution, the formic acid, the acetic acid, the lignins and the hemicelluloses, constituting a second cosubstrate capable of then being hydrolysed after separation of the acids and of the lignins.

15. The process of claim 1, wherein said step iv) produces bioethanol.

* * * * *